United States Patent [19]

Begemann et al.

[11] Patent Number: 4,972,834
[45] Date of Patent: Nov. 27, 1990

[54] PACEMAKER WITH IMPROVED DYNAMIC RATE RESPONSIVENESS

[75] Inventors: Malcolm J. S. Begemann, Yelp; Willem Boute, Doesburg; Marijn van Gemert, Nijmegen, all of Netherlands

[73] Assignee: Vitatron Medical B.V., Dieren, Netherlands

[21] Appl. No.: 252,643

[22] Filed: Sep. 30, 1988

[51] Int. Cl.$^5$ ............................................. A61N 1/365
[52] U.S. Cl. .............................. 128/419 PG; 128/703
[58] Field of Search ................ 128/419 PG, 696, 703

[56] References Cited

U.S. PATENT DOCUMENTS

| | | | |
|---|---|---|---|
| 4,228,803 | 10/1980 | Rickards | 128/419 PG |
| 4,305,396 | 12/1981 | Wittkampf et al. | 128/419 PG |
| 4,313,442 | 2/1982 | Knudson et al. | 128/419 PG |
| 4,493,325 | 1/1985 | Hartlaub et al. | 128/419 PG |
| 4,527,568 | 7/1985 | Rickards | 128/419 PG |
| 4,644,954 | 2/1987 | Wittkampf et al. | 128/419 PG |
| 4,688,573 | 8/1987 | Alt | 128/419 PG |
| 4,712,555 | 12/1987 | Thornander et al. | 128/419 PG |
| 4,716,887 | 1/1988 | Koning et al. | 128/419 PG |
| 4,730,619 | 3/1988 | Koning et al. | 128/491 PG |
| 4,803,987 | 2/1989 | Calfee et al. | 128/419 PG |

OTHER PUBLICATIONS

Vitatext, publication of Vitatron Medical B.V., pp. 6–17, Oct. 1987.
Abstract, "Improved Algorithm in TX Pacemakers, Preliminary Clinical Experience," *PACE*, vol. 10, p. 1210, Sep.–Oct. 1987.
Abstract, "Introduction of a New Generation of QT-Driven Rate Responsive Pacemakers," *PACE*, vol. 10, p. 1208, Sep.–Oct. 1987.
Abstract, "Electrophysiological Basis of a New Algorithm for the TX Pacemaker", *PACE*, vol. 10, p. 1207, Sep.–Oct. 1987.
Abstract, "Automatically Adjusting Slope Setting for the QT-Sensing Pacemaker—Initial Clinical Evaluation," *PACE*, vol. 10, p. 1207, Sep.–Oct. 1987.

*Primary Examiner*—Lee S. Cohen
*Assistant Examiner*—Kennedy J. Schaetzle
*Attorney, Agent, or Firm*—Woodcock Washburn Kurtz Mackiewicz & Norris

[57] ABSTRACT

A rate adaptive pacemaker system, and method of operation, is provided which has a pacemaker which generates pacing pulses at a controlled pacing rate as a function of at least one monitored patient variable. The correlation of pacing rate with the patient variable is nonlinear, or dynamic, and is adapted to actual patient conditions. The value of the relationship between the pacing rate and the monitoring variable is determined at the lower rate limit and the upper rate limit, and the dynamic characteristic between these limits is automatically adjusted.

22 Claims, 7 Drawing Sheets

SLOPE = $\frac{\Delta P.I}{\Delta Q.T}$

PACEMAKER WITH IMPROVED DYNAMIC RATE RESPONSIVENESS

FIELD OF THE INVENTION

This invention relates to cardiac pacemakers and, in particular, rate responsive pacemakers having means for adapting the correlation between a monitored patient variable and indicated pacing rate as a function of sensed patient history.

BACKGROUND OF THE INVENTION

Single chamber rate responsive pacemakers have been available in the pacing community for about a decade now. Since their introduction, rate responsive pacemakers have gained increased acceptance as providing an improved response to the patient's physiological need. Atrial-based pacers, i.e., atrial synchronous or atrial sequential pacers, were probably the first form of rate responsive pacemaker. However, such atrial-based pacemakers, including DDD pacemakers, are dual chamber devices that require a second lead to be positioned in the atrium, and further are not satisfactory for patients with certain cardiac conditions. A number of indicators other than the atrial rate have been suggested as suitable for determining the optimal pacing rate in patients where DDD pacing is not indicated. The first commercially available form of single chamber rate responsive pacemaker was the QT driven rate responsive pacemaker, marketed by the assignee of this invention. See U.S. Pat. No. 4,228,803, to Rickards. Subsequently, other pacemakers utilizing other monitored variables have been introduced commercially, the best known example being the Activitrax model manufactured by Medtronic, Inc.

Even though there are now pacemakers utilizing a number of respective different monitored variables for determining rate, the general structure of the rate responsive pacemaker is common and generic. Any rate responsive pacemaker incorporates a sensor adapted to sense a patient's variable which indicates, or reflects the patient's needs at any given moment, and which provides both quantitative and progressive information. For example, in the QT pacemaker, the sensor is the same lead that delivers the pacing pulses. Following delivery of a pacing pulse, it senses the stimulus-evoked T-wave, and provides an electrical signal which can be compared in the time domain to the stimulus pulse, thus providing the QT time interval information. Whatever sensor is used for sensing an indication of physiological demand, in order to be useful in a modern implantable pacemaker, it must have long term stability and reliability.

The general structure of a rate responsive pacemaker also includes a means for carrying out an algorithm by which the pacemaker determines the indicated pacing rate on the basis of information delivered by the sensor. The function of the algorithm is to provide a correspondence, or correlation between the sensed indicator variable and the pacing rate, so that the pacemaker is accurately responsive to the monitored information.

Lastly, of course, a standard multi-programmable single-chamber pacemaker is utilized. For purposes of illustrating the preferred embodiment, this specification references the Vitatron TX pacemaker (QT driven). See U.S. Pat. Nos. 4,228,803; 4,305,396; 4,644,954; and 4,527,568, which are incorporated herein by reference. See also the publication Vitatext, October, 1987, published by Vitatron Medical B.V.

Using the QT driven rate responsive pacemaker as an example, the algorithm determines the change in pacing rate per ms change in the stimulus-T interval, which is defined as the slope. Correct programming of the slope, and accurate processing by the pacemaker are seen to be crucial factors in obtaining optimal pacemaker functions. Initially, the slope, or relationship between QT interval and pacing rate, was fixed. Recent investigations into the relationship between the QT interval and the desired pacing rate have indicated that the slope should be variable, i.e., there should be means for automatic adaptation of the slope as a function of patient history, in order to maintain optimal long-term rate response, even under changing circumstances. This finding reflects a long felt need of rate responsive pacemakers, namely that the correlation data between the monitored patient variable or variables and the desired pacing rate generally should be dynamic and subject to variation from patient to patient and as a function of patient history. Accordingly, there is a need in rate responsive pacemakers for implementation of automatic adaptation of the slope, or a pacing rate/indicator variable characteristic.

SUMMARY OF THE INVENTION

It is an object of this invention to provide a rate adaptive pacemaker having an improved manner of determining and implementing the correlation between the sensed patient indicator variable and selected pacing rate.

It is another object of this invention to provide a rate adaptive pacemaker having rate control means for dynamically adjusting the control of pacing rate as a function of a monitored patient variable.

It is another object of this invention to provide an improved means and method of adapting pacemaker rate responsiveness to the patient in which a rate responsive pacemaker is implanted.

It is a further specific object of this invention to provide a QT driven pacemaker having a dynamic characteristic of pacing interval vs. QT interval, i.e., slope, and for adjusting the slope as a function of patient history.

In accordance with the above objects, there is provided an adaptive rate responsive pacemaker which has a generator for generating pacing pulses at a controlled pacing rate, means for monitoring at least one patient variable correlative of desired heart rate, e.g., QT interval, and means for adjusting the rate so that the correlation of the pacing rate and the patient variable is adaptive to actual patient conditions. In practice, the value of the slope at a lower rate limit (LRL) and upper rate limit (URL) is corrected in accordance with patient conditions or history, and the dynamic slope between LRL and URL is automatically adjusted to fit in between those limits. An external programmer can be used to make changes in the parameters that affect rate, such as LRL and URL.

DESCRIPTION OF THE PREFERRED EMBODIMENTS

Figure 1:
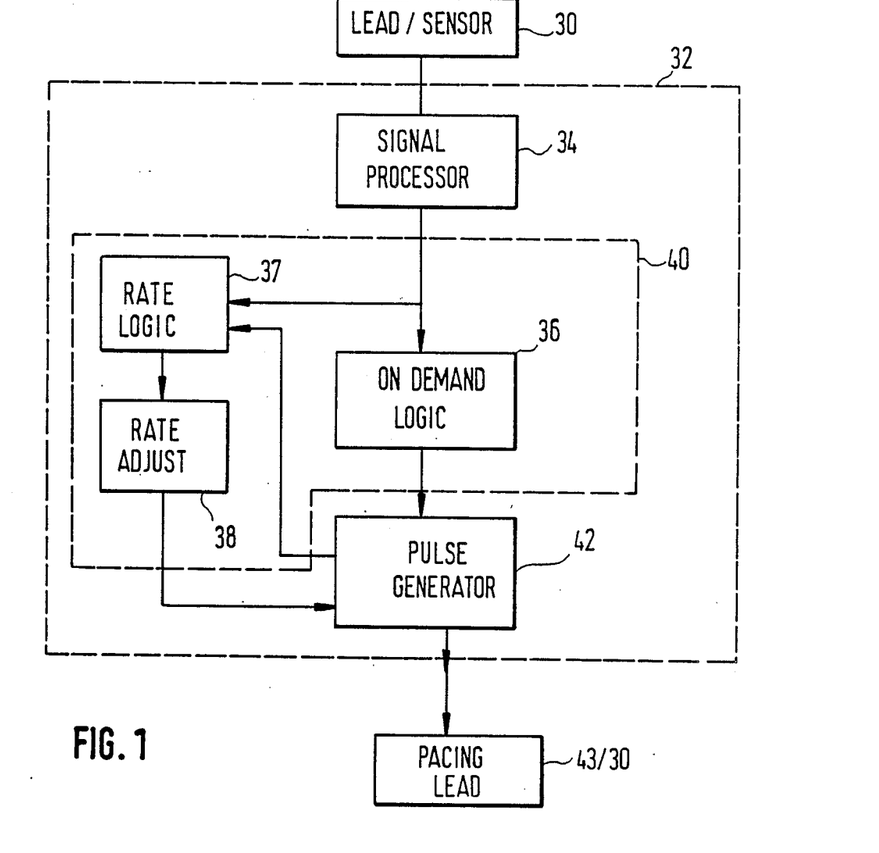
FIG. 1 is a block diagram of a rate adaptive pacemaker in accordance with this invention.

Referring now to FIG. 1, there is shown a block diagram indicating conceptually the components of a rate adaptive pacemaker. A lead or sensor 30 is represented for deriving patient information. As used in this invention, one or more sensors may be utilized to detect one or more patient variables indicative of patient demand for heart rate. In the preferred QT driven embodiment, the sensor 30 is integral with the lead going into the ventricle, and senses the T wave response, whereby the QT interval may be obtained. Other sensors for sensing other patient variables, including mechanical movement, respiration rate, blood pH, temperature, etc. are known in the pacing art for use in rate responsive pacers, and may be utilized as an embodiment of this invention. The input from the sensor or sensors 30 is communicated to the implantable pacemaker 32. The sensor information is passed through conventional signal processing 34 to place it into suitable form for further use in the logic circuitry. The output of the signal processing circuit, in the QT embodiment of this invention, is transmitted to on demand logic circuitry 36, for generating control signals for controlling the generation of stimulus pulses in the absence of natural heartbeats, in a manner well known in the art. The output of on demand logic block 36 is transmitted to pulse generator 42, which provides the pacemaker output pulses. The output pulses are delivered to a pacing lead 43, which for the QT case is lead 30.

In the QT preferred embodiment, the output of signal processing circuit 34, which includes indications of the T wave, is inputted to rate logic circuit 37 for determining the timing of the T wave relative to the delivered pulse signal, the timing of the latter being is provided from pulse generator block 42. The rate logic circuitry also provides means for determining the desired pacing rate as a function of QT, or other sensed variable, in a manner described in more detail hereinbelow. The output of rate logic circuit 37 is transmitted to rate adjust circuit 38, which generates an appropriate control signal which is transmitted to pulse generator 42, to control generator 42 to deliver pulses at a rate, or pacing interval, corresponding to the output of rate logic circuit 37. In the case of the QT driven pacemaker, rate logic means 37 preferably includes stored data correlating values of QT interval with respective values of pacing interval, the ratio of which is defined as "slope." Thus, for a given sensed QT interval, rate logic block 37 provides an output that corresponds to a determined pacing interval at which the pacemaker paces the patient in response to the detected QT interval. For other embodiments which incorporate sensors for one or more other indicator values, equivalent means are incorporated for generating the rate logic and rate adjust circuits. As indicated at 40, the functions of blocks 36, 37, and 38 may be carried out in a CPU or microprocessor, as disclosed in one or more of the referenced patents. The microprocessor 40 also contains memory for storing parameter data, which data is used in determining rate in a manner discussed hereinbelow.

Figure 2:
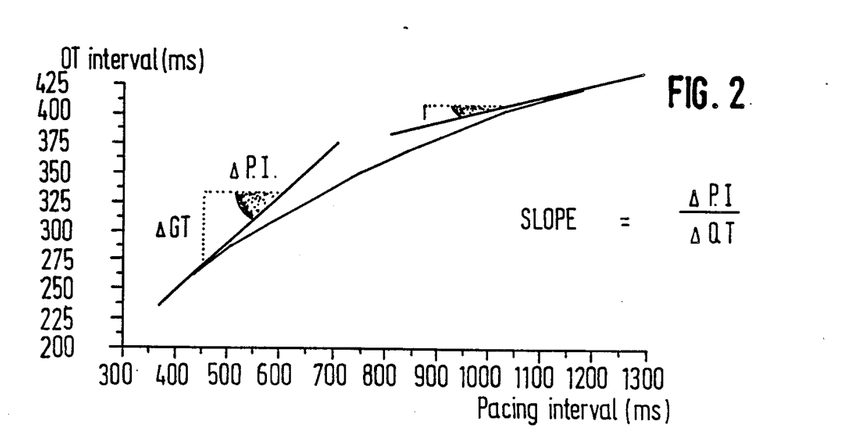
FIG. 2 is a graph of QT vs. pacing interval (P.I.) for a specific embodiment of this invention.

Referring now to FIG. 2, there is shown a graph depicting generally how QT interval (ms) varies as a function of pacing interval (ms) due to physiological variables. As seen, there is depicted a rate-dependent relationship between QT interval and pacer interval. It has been determined empirically that QT interval as an indicator is influenced by both heart rate alone (which can be seen when the patient is at rest) and also by patient demand, e.g., when a patient undergoes exercise. Stating it alternatively, the relationship between pacing interval and QT interval is a function of two factors, i.e., patient metabolic demand such as induced by exercising, and also the heart rate itself. The resultant graph is seen to be nonlinear, representing a non-linear slope which is defined as incremental change in pacing interval per incremental change in QT. It is seen that at high pacing intervals, corresponding to a lower rate, the variation of slope is greater, whereas at lower pacing intervals (corresponding to higher rates) the variation of slope is less. This results from the fact that when a higher rate is implemented by the pacemaker, the shorter P.I. tends to induce a further decrease in QT beyond what was initially indicated by the body's demands. In practice, the degree of QT interval shortening is least at long pacing intervals. If this is not compensated for, there may result a delay before a significant increase in pacing rate is seen after the commencement of exercise in some patients. Further, by lowering the slope as rate is increased, the pacemaker is not driven directly to URL too quickly.

Figure 3A:
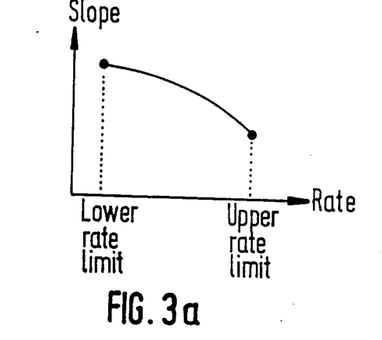
FIG. 3(a) is a representation of slope vs. rate for one embodiment of this invention.
Figure 3B:
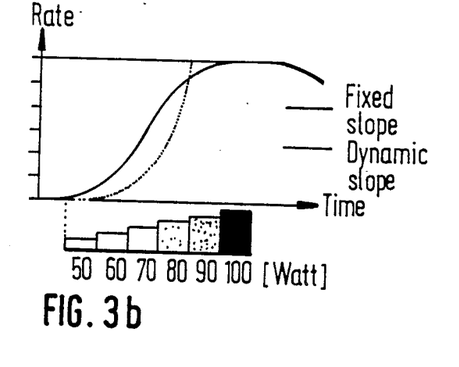
FIG. 3(b) is a graph of controlled rate vs. time through an episode of patient work (exercise), in accordance with a preferred embodiment of this invention.

Referring now to FIG. 3(a), there is shown a representation of slope vs. rate for the QT driven embodiment of this invention, varying from LRL to URL. This graph represents basically the same information as set forth in FIG. 2, and shows that the desired slope is not constant, but is variable or dynamic. Note that the slope at LRL is higher than at URL, meaning that at lower rates the change in pacing interval for incremental changes in QT is made greater, while it is less at higher rates. Referring to FIG. 3(b), there is shown a representation of pacemaker controlled rate as a function of time for the QT driven embodiment, where the patient is undergoing exercise as indicated. Two curves are shown, one for a fixed (constant) slope, and one for a nonlinear or dynamic slope. Note that the fixed slope reaches URL before the dynamic slope, which means that for fixed slope response the change of rate is not spread out as well over the period of exercise as it is for the dynamic slope. Thus, for the fixed slope curve, the patient reaches URL much before the exercise limit is reached, whereas for the dynamic slope the approach to URL is extended such that there is a variation in rate which more accurately corresponds to the demand of the patient.

Figure 4A:
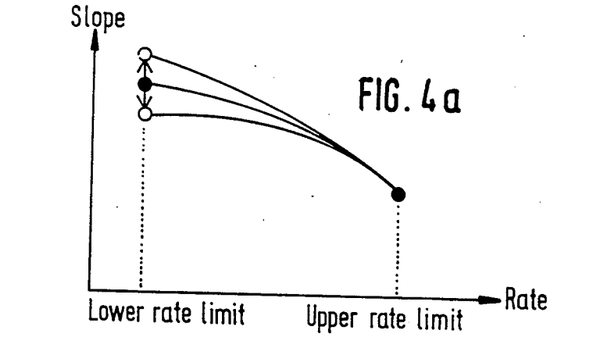
FIG. 4(a) is a graph representing slope vs. rate for a preferred embodiment of this invention, showing adjustment of slope at the lower rate limit.

Referring now to FIG. 4(a), the implemented variation in slope at the lower rate limit (LRL) is illustrated in a general manner for a pacemaker system that is rate-responsive. In a preferred embodiment, the slope at the programmed LRL is automatically measured once a day presumably when the patient is at rest. This is accomplished in the QT embodiment by having the pacemaker determine the relationship between the QT interval and the pacing interval at rest, when the following two conditions are fulfilled: (a) the pacemaker is pacing at LRL, and the patient is therefore resting or sleeping; and (b) the pacemaker's internal 24-hour clock indicates that it is nighttime. The relationship, or slope, is determined by incrementally changing the pacing rate about LRL, and detecting the change in QT, so as to get a measurement of slope at about LRL. This value determines the actual desired slope at LRL, and if such slope is different from the previous maximum slope, the slope at the LRL is automatically reprogrammed. Preferably, in order to avoid the possibility of a sudden, harsh charge in the programmed slope at LRL, the algorithm only allows the slope to be adjusted in small steps, as indicated in FIG. 4(a). Having determined the slope at LRL, the remainder of the slope curve can be determined by the slope parameters, including the slope at URL, as illustrated.

In general, the slope can be calculated as a function of interval (pacing interval, or escape interval) in a variety of ways. For example, the change in pacing interval for a certain change in sensor input(s), i.e., slope, may be a simple formation of pacing interval. Thus, $\Delta$Esc. Int./$\Delta$QT=f (Esc. Int.)

Figure 4B:
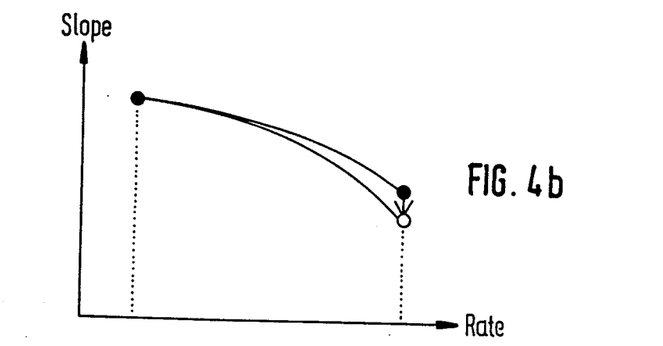
FIG. 4(b) is a graph of slope vs. rate for a preferred embodiment of this invention, showing adjustment of slope at upper rate limit.

Alternately, slope may be a function of change in the sensor input value (i.e., $\Delta$QT), or a function of both the pacing interval and change in sensor input. The algorithm for determining slope is not limited. In the preferred QT embodiment, the function is linear:

Slope=$\Delta$QT/$\Delta$Int.=A+B (60,000/LRL-Esc. Int.)
where $\Delta$Int.=LRL Interval-Esc. Interval, B=curve factor (primary determinant of slope at URL) and A=slope at LRL Referring to FIG. 4(b), there is shown a generalized illustration of slope adjustment at the Upper Rate Limit (URL). The slope at the programmed URL is checked whenever the patient exercises strenuously, and therefore drives the pacing rate to URL. Once the pacing rate has reached the programmed URL, the pacemaker continues to monitor the QT interval. Any further decrease in QT interval indicates that, although the URL has been reached, the patient is able to perform an even higher level of exercise, indicating that URL has been reached prematurely for that patient. In such a situation, the pacemaker responds by decreasing the slope at URL by one step, or increment. By thus lowering the slope at URL, patient exercise automatically results in a smoother rate increase towards URL on subsequent exercise episodes.

Figure 4C:
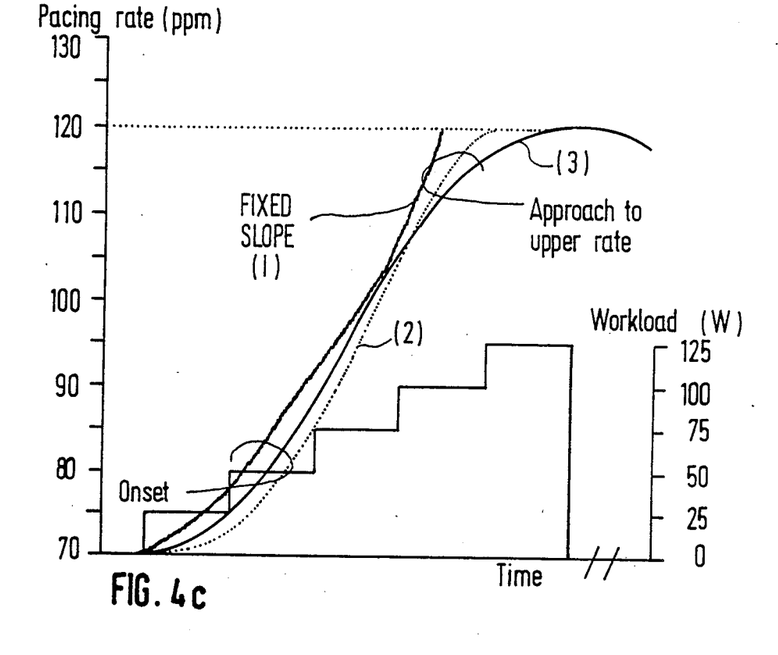
FIG. 4(c) is a graphical representation of pacing rate vs. time, during indicated patient workload, showing the response of the pacemaker for different slopes.

Referring now to FIG. 4(c), there is shown a representation of the effect of automatic adaptation of the variable, or dynamic slope. FIG. 4(c) illustrates pacing rate (ppm) vs. time of exercise, for three different calculations of slope. For slope 1, corresponding approximately to a fixed slope, pacing rate responds slowly at LRL but rises most quickly to URL as a function of workload. Dynamic slopes 2 and 3 illustrate respective progressively optimized dynamic slopes for bringing pacing rate from the lower limit to the upper limit as a function of workload over time. In a preferred embodiment the slope at LRL can be programmed to one of three different levels of the calculated maximum slope, resulting in a fast, gradual or smooth onset of the rate response; while slope at URL can also be programmed to one of three levels, resulting in a fast, gradual or smooth approach to the upper rate limit.

It is noted that for the QT preferred embodiment, whenever the pacemaker is inhibited it is unable to obtain any information concerning patient metabolic demand. This difficulty is overcome by providing that after every sixteenth successive inhibition the escape interval is set shorter than the last spontaneous interval by a predetermined amount, so as to overdrive the natural heartbeat and produce a stimulus. The evoked QT interval is then measured so that information indicating the required heart rate can be obtained. This information is then compared with the spontaneous heart rate and, if necessary, the pacemaker is adapted to pace at a higher rate as determined by the evoked QT interval. For embodiments utilizing patient variables not directly derived from the sensed heartbeat signal, comparison between the pacing rate and the monitored variable may be made continuously.

Figure 5A:
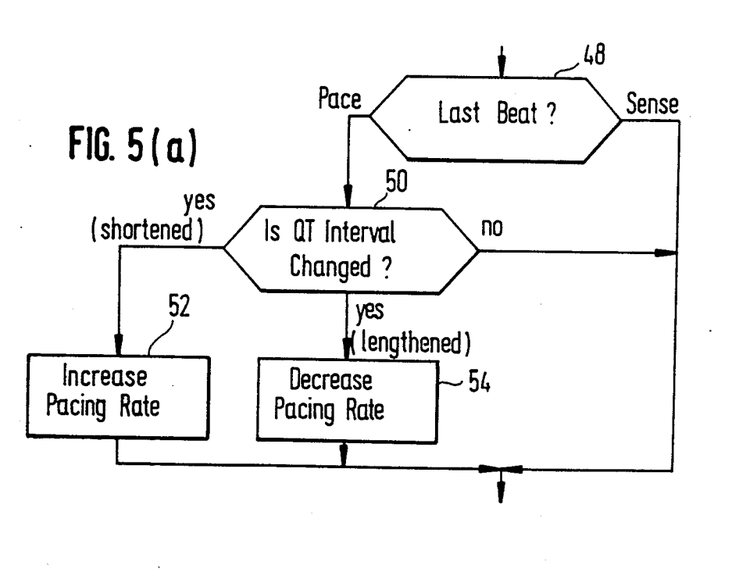
FIG. 5(a) is a block diagram of a basic algorithm for the QT driven preferred embodiment of this invention.
Figure 5B:
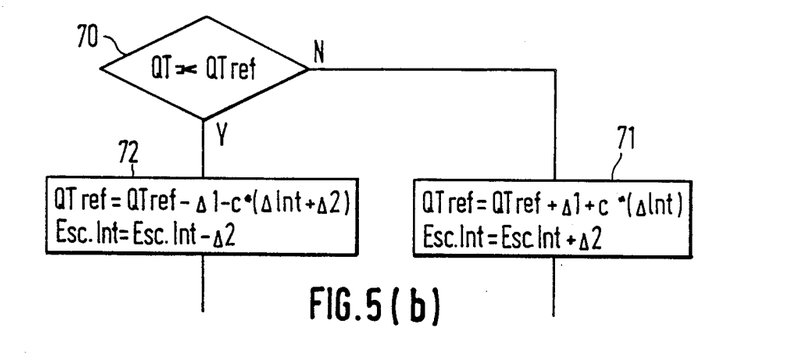
FIG. 5(b) is a flow diagram for determining the pacing rate for one embodiment of this invention.

Referring now to FIG. 5(a), there is shown a basic algorithm for adjusting the pacing rate as a function of QT interval in the QT preferred embodiment of this invention. This algorithm is preferably carried out in a software embodiment. As indicated at block 48, a determination is made whether the last beat was a paced or a sensed beat. If sensed, there is no adjustment of pacing rate and the subroutine exits. If the last beat was paced, the pacemaker then determines, at block 50, whether QT interval has changed from the last cycle. If no, no change is indicated and the subroutine exits. If yes, it is determined whether the QT interval has shortened or lengthened. If shortened, then the pacing rate is increased incrementally, as indicated at block 52. If lengthened, then the pacing rate is decreased incrementally, as indicated at block 54. The determination of pacing rate (or Esc. Int.) and the QT reference may be made in accordance with the simplified flow diagram of FIG. 5(b). Each time QT is measured, it is compared to QT ref. This comparison determined whether QT has shifted. If QT is not equal to or less than QT ref., the program branches to block 71. Here, QT ref. is updated by the addition of a predetermined number of milliseconds ($\Delta$1), as well as an increment which is equal to B ($\Delta$Int.). The escape interval is incremented by adding $\Delta$2, and other predetermined number of milliseconds. It is to be noted that the slope at LRL, A, is equal to $\Delta$1/$\Delta$2. If the comparison at block 70 is yes, both the QT ref. and escape interval values are decremented, as there indicated.

Figure 6A:
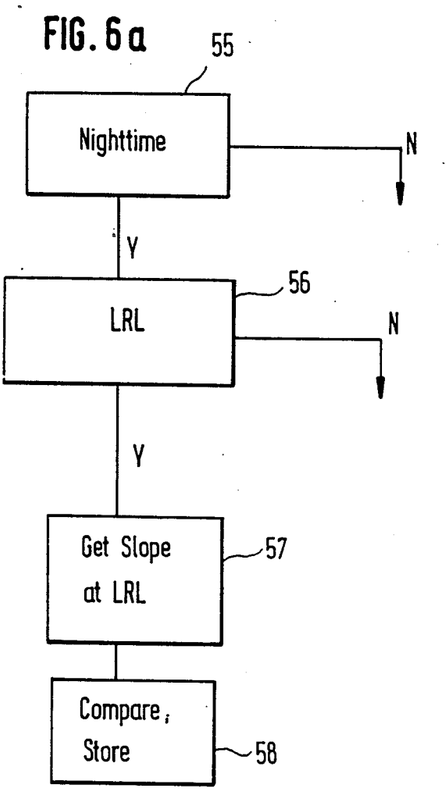
FIG. 6a is a flow diagram of a pacemaker algorithm for adapting slope at LRL, for the QT embodiment.

Referring now to FIG. 6a, there is shown a simplified block diagram of a subroutine for adjusting the value of the slope at LRL. As indicated at block 55, the pacemaker checks its clock and determines whether it is nighttime. If this condition is met, the pacemaker then determines at 56 whether the pacing rate is at LRL. If yes, then the pacemaker determines the slope at LRL (57). This is done by incrementally changing the pacing interval, with respect to LRL, and observing the change in QT. If the slope at LRL (A) is different, the new slope is stored in memory (58).

Figure 6B:
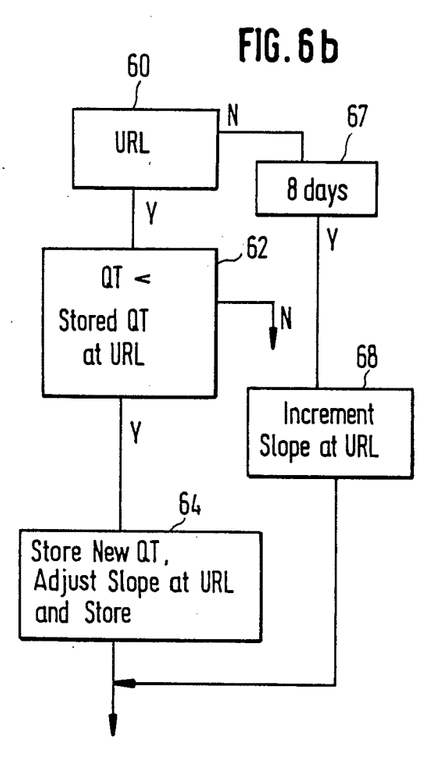
FIG. 6(b) is a flow diagram of a pacemaker algorithm for adapting slope at URL, for the QT embodiment.

Referring to FIG. 6b, there is shown a simplified block diagram of a subroutine for checking the value of the slope characteristic at URL. At block 60, it is determined whether the pacemaker has been operating at URL. If yes, A determination is carried out, as shown at block 62, of whether the QT interval is now less than the old stored QT interval for URL. Thus, for heart cycles after reaching URL, the pacer monitors additional changes in the sensor value, and determines if continued exercise has caused further change in the sensor value. If no, then the routine exits, there being no indication that an adjustment is desired. However, if the answer is yes, indicating that further exercise has caused even further change in QT or other sensor value, then at block 64 the new value of QT is stored; the slope at URL is recalculated to correspond to the lesser value of QT at URL. Returning to block 60, if the pacemaker is not at URL, a determination is made at block 67 as to whether URL has been reached within the last 8 days (or other predetermined time). If yes, then the slope at URL is incremented at block 68, reflecting the fact that the patient has a history of more moderate daily activity, such that slope at URL should be incremented. The slope is incremented so that the pacing rate reaches URL corresponding to the more moderate exercise level of the patient.

In practice, when a rate responsive pacemaker is implanted and the rate responsive mode is switched on, the slope data settings are initially automatically set to low values. By the adaptation techniques as set forth above, the dynamic slope rises to its optimal form, but this may take several days to reach. Accordingly, a fast learning procedure can be implemented, which essentially eliminates the initial adaptation phase. For the fast learning procedure, there are two stages. There is a rest measurement stage, during which the pacemaker gathers data on the slope value at LRL when the patient is at rest, whether or not it is nighttime. This value of slope data is programmed as the slope at the lower rate limit, and is the maximum value of slope. The patient is then put through a second stage where there is an exercise measurement, e.g., the patient is caused to perform an exercise stress test. During this stage, the pacemaker is driven to upper rate limit, and calculates the slope corresponding to the upper rate limit. With the two limit values of slope thus determined and stored, the optimal dynamic slope is filled in for all values of pacing rate between LRL and URL. Of course, subsequent adaptation may well occur, but the fast learning capability quickly brings the pacemaker quickly to a substantially optimum slope characteristic.

Figure 7:
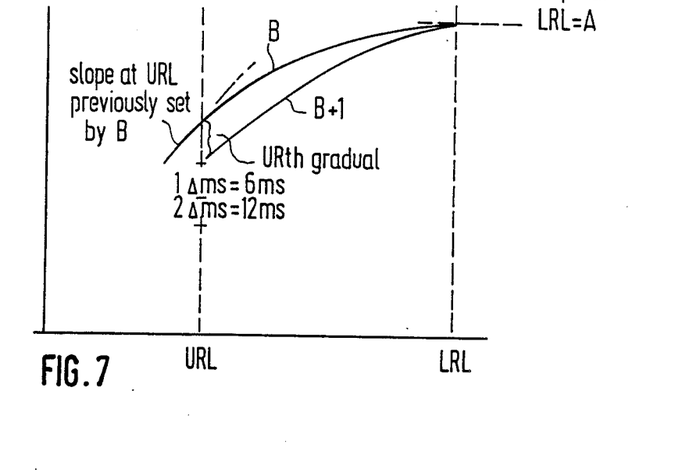
FIG. 7 is a graph illustrating the manner of changing slope curve factor B as a function of the URL threshold setting (URth)

In determining when and under what circumstances the slope is to be adjusted at URL, the pacemaker is programmed with a setting referred to as upper rate approach threshold, or URth, which is a threshold change in QT that must be determined before the slope is automatically adjusted. Thus, in referring to FIG. 7, it is seen that if the curve value of slope B is changed by one unit (e.g., from 20 to 21), this would correspond to a certain change in QT at URL. This difference of necessary sensor input QT input that is required to exactly correspond to changing the slope curve factor B one step (for a given LRL and URL) is designated the "gradual" URth. In a preferred embodiment, there are three programmable settings for the URth, the "standard" setting being the same as for gradual, but having an extra 6 ms QT change added; and the fast threshold being gradual plus 12 ms. Thus, if the standard URth setting is adopted, the change in QT due to exercise to cause a change in B of one, after the patient has reached URL, must be 6 ms more than would correspond to changing the curve factor B by one. Of course, within the scope of the invention there can be any number of programmable values of URth, to provide desired flexibility and adaption of the curve to respond to patient exercise needs.

Alternatively, the slope may be adjusted for a sensed change at URL by keeping B fixed, but changing the A value. Thus, it is to be understood that the manner of making changes to respond to sensor data when at URL is not limited to the specific embodiment illustrated.

Likewise, at the LRL end of the slope, the slope A at LRL is also adjustable to one of preferably three settings. It is to be recalled that at nighttime, the slope at LRL is measured, representing the change in QT found to correspond to an incremental change in pacing interval. This nighttime measured slope is designated $A_n$. In the preferred embodiment, an onset setting $O_n$ is utilized for determining when the measured value of $A_n$ differs from the old programmed A value by a sufficient amount to justify a change in the A value. Thus, assume that the value of $O_n$ can be $+2$, O or $-2$, corresponding to gradual, standard, and fast settings respectively. The measured value of $A_n$ plus the onset value are added and compared to the present stored value A, the comparison indicating whether a new value of A should be determined by incrementing or decrementing A by one. For example, if An is measured to be 15 and $O_n$ is $+2$, the combined value of 17 is compared to the stored value of A. If A had a value of 20, then the sensed 17 is less than 20, and a new value of A is found by decrementing A by one unit.

Figure 8:
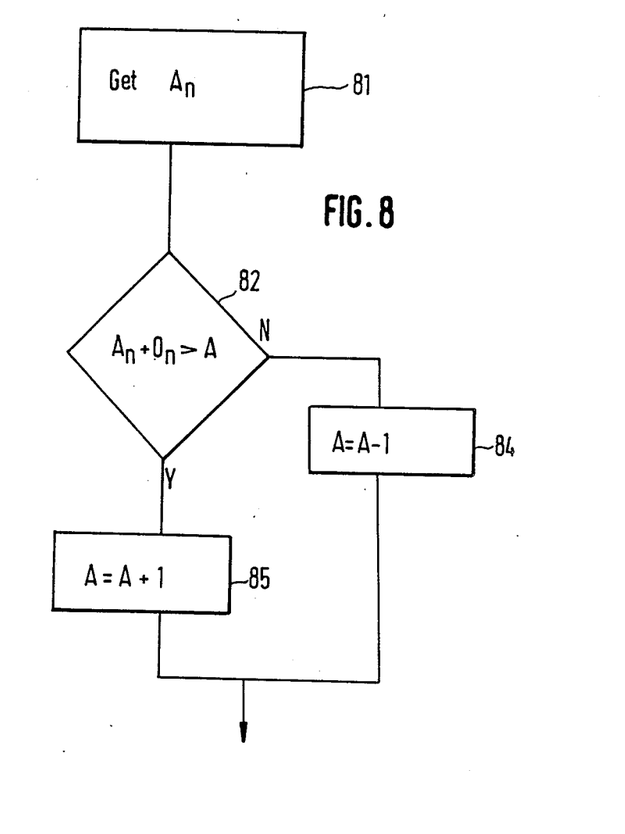
FIG. 8 is a simplified flow diagram illustrating how the onset parameter ($O_n$) is used in automatically adapting the slope at LRL (A)

Referring to FIG. 8, the logic of automatic slope variation at LRL is shown. The value of $A_n$ is obtained at nighttime (81). The value of $A_n$ is added to the $O_n$ setting, and compared to the present value of A (82). If the combined value is not greater than A, the program branches to block 84 and decrements A by one unit. If the combined value is greater, then the value of A is incremented by one unit at block 85. It is noted that the onset value can have any number of different values, depending upon the flexibility desired for slope adjustment. Preferably, if $A_n = A$, then there is no change.

The pacemaker system of this invention takes into account the fact that slope settings have to be recalculated when other parameters are changed. Thus, when LRL is reprogrammed by an external programmer, the slope at the new LRL has to be recalculated. Also, the URth setting is a function of the new LRL. In order to produce the new slope values, the pacemaker utilizes a reference curve which is stored in its memory and which contains all of the parameters from which slope is determined, namely LRL; slope A at LRL; onset On for determining changes in slope at LRL; URL; slope curve factor B (which determines slope at URL); and URL approach (URth). This reference curve is updated only automatically by the programmer upon interrogation, and then only once a day or when it does not correspond with the actual curve, as happens in response to exercise. In general, the only exceptions to this rule are during the fast learn procedure, which also adjusts the reference curve, and when upon interrogation the pacemaker indicates that it has been initialized.

Thus, in the present embodiment, the pacemaker contains two sets of data, referred to as "actual" and as "reference". The actual curve parameters are A and B, and the actual settings are LRL, URL, $O_n$ and URth. The reference data contains six pieces of data corresponding to these same parameters. When the pacemaker is in the automatic slope adjustment mode, the actual curve, which controls pacemaker rate, is automatically adapted, but the reference curve information remains the same.

The preferred embodiment of this invention also provides for operating the pacemaker in a "fixed curve" mode, whereby the slope is not adaptable as a function of determinations made at LRL or URL. In this mode, while the curve cannot be automatically adjusted, it can be changed manually by external programming, to change the slope in a predetermined small range. The programmer limits the changes to two steps from the reference curve per day, i.e. either A or B can be changed, but no more than by two steps per day. After each day, the reference curve can again be adjusted upon interrogation by the programmer, but again only by two steps in each direction.

Figure 9:
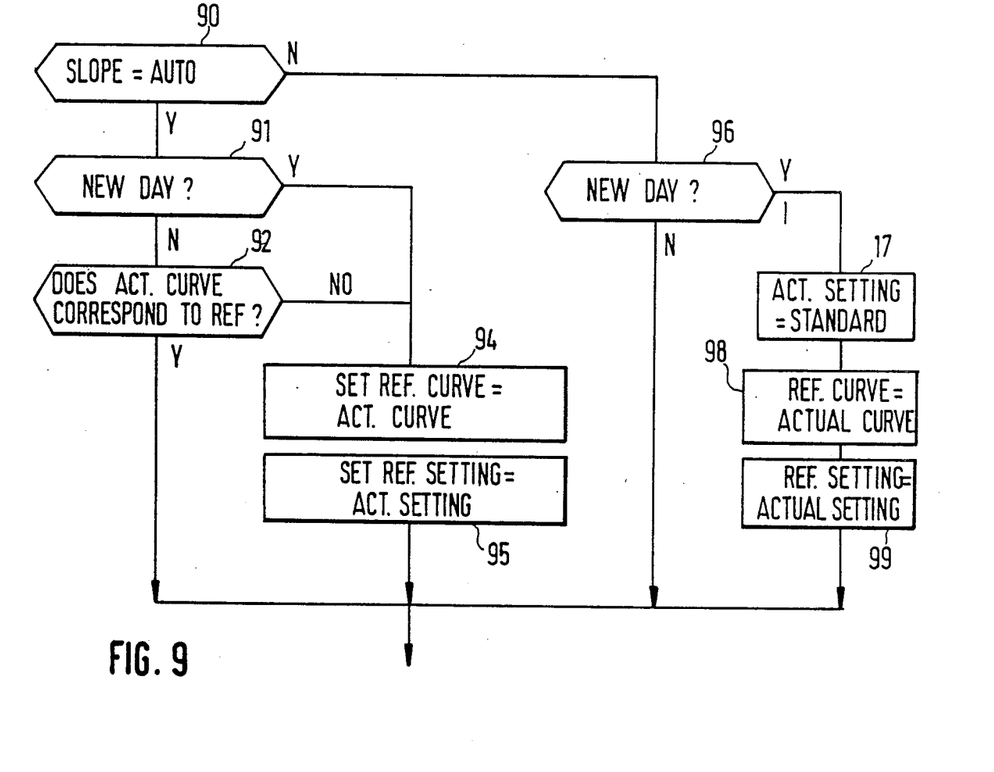
FIG. 9 is a simplified flow diagram of an embodiment of the invention wherein the pacemaker reference curve is changed under certain conditions.

Referring now to FIG. 9, there is shown a block diagram indicating how the pacemaker of this invention sets limits on the user's ability to change the reference curve data each day. In this generalized flow diagram, it is first determined whether the pacer is in the auto slope mode. If yes, at 91 it is determined whether it is a new day i.e., has there already been a change during this day? Thus, if there has already been one programming episode during the day, the answer is no, and the program branches to block 92. At 92 it is determined whether the actual curve corresponds to the reference curve, i.e. whether the actual curve could be derived from the reference settings of A and B. If the actual curve does so correspond, the program exits. If it doesn't, this is the one exception to permitting updating even if it is not a new day, since then there is an indication that a curve parameter has been automatically changed due to exercise. In this event, as well as when there is a new day determined at 91, the program branches to block 94, where the actual curve (slope parameters A, B) is put into the reference curve. Then at block 95 the actual setting parameters (onset, URth, LRL and URL) are put into the reference setting. Thus, in exiting after 94 and 95, the reference data has been completely updated to correspond to the actual data.

Referring to block 90, if the slope is fixed, the program branches to block 96 where again it is determined if it is a new day. If no, the program exits directly, thus preventing additional changes for that day. If it is a new day, the program branches to block 97 where the actual settings are set equal to standard, i.e. both onset and URth are set to zero steps. The program then continues to 98 where the actual curve is placed into the reference curve, and then to block 99 where the actual settings are placed into the reference settings, thus providing a change in the reference curve in accordance with the settings that have been determined by the operator.

Figure 10:
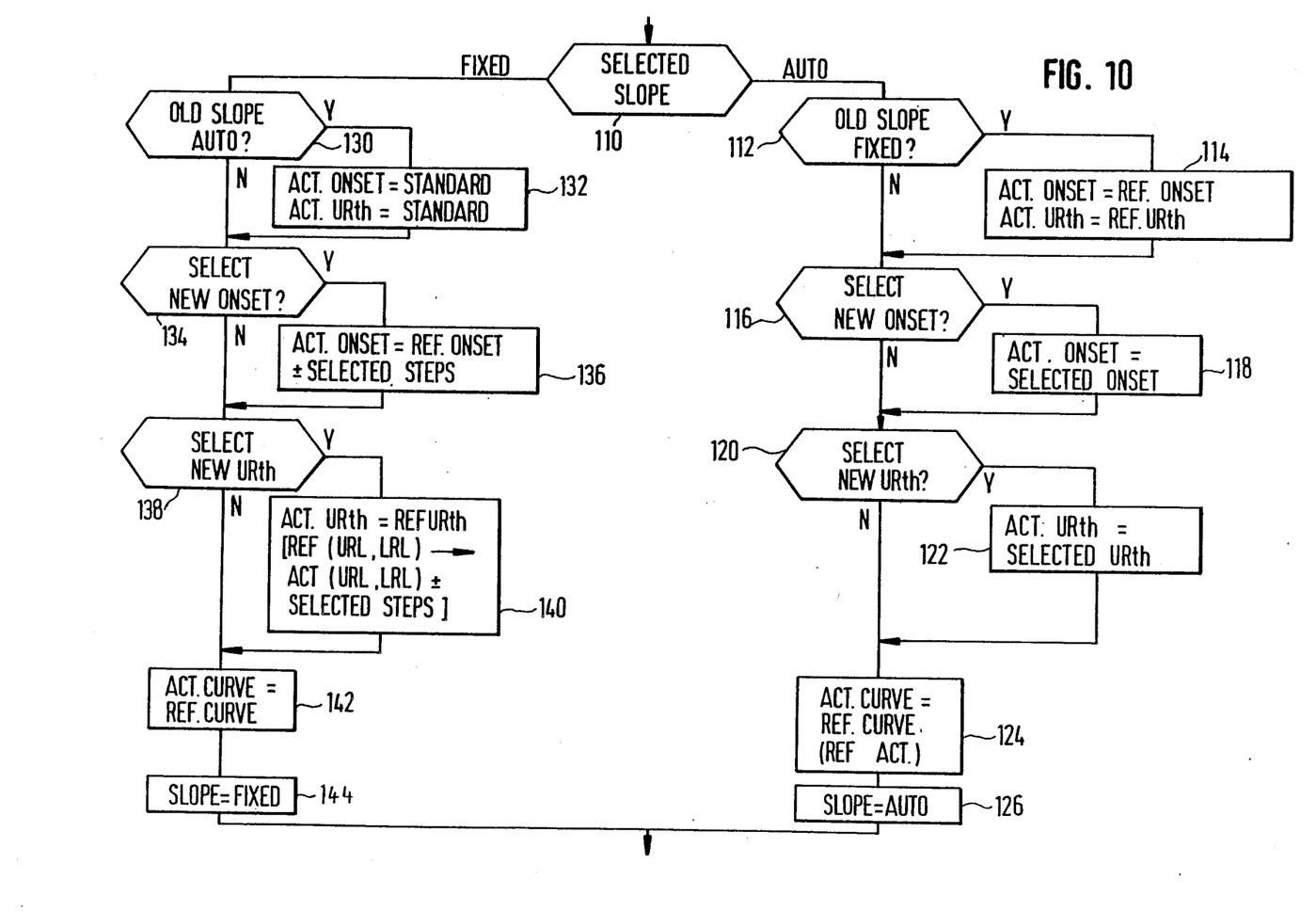
FIG. 10 is a flow diagram illustrating external programming of the pacemaker for changing of the slope.

Referring now to FIG. 10 there is shown a more detailed flow diagram for carrying out the changes during external programming. It is noted that a change in LRL or URL may have already been programmed. The program starts as indicated at block 110, where the operator makes a decision as to whether to be in the fixed or automatic mode of adjusting slope. If auto is chosen, this means that it is desired to be in auto slope adjustment when the programming is through, and the path to the right is taken. As shown at 112, the programmer checks to see whether the old, or prior slope had been fixed. If yes, this means that the program must make changes in accordance with the desire to go from fixed to auto, and the program branches to block 114. There, the actual onset parameter is set equal to the reference onset parameter, i.e., whatever onset information is in reference storage is put into storage corresponding to the actual curve. Also, a new value of QTth is derived from the reference data, and placed in "actual" storage. Thus, if LRL or URL had been changed, a new corresponding reference QTth is calculated, and this actual value is made equal to this new value.

The program then branches to block 116. Note that if the pacemaker had already been in auto slope mode, the program would go directly from 112 to 116. At block 116, the operator makes a determination as to whether a new onset is to be selected. If no, the program proceeds directly to block 120. However, if a new onset is desired, the program branches to 118, where the selected onset is programmed and put into storage as the actual onset. Proceeding then to block 120, a similar decision is made as to whether a new QTth is to be selected. If no, the program proceeds directly to block 124, but if yes, it proceeds to block 122. There the operator inputs the new desired QTth, which is stored as the actual QTth data. Proceeding to block 124, the actual curve derived from the reference curve is updated, and the updated reference curve, i.e., the A and B slope parameters are calculated from the reference curve to give the pacer the actual curve. Then, at 126, the pacemaker is put into auto mode and exits the routine.

Returning to block 110, if the operator wants the pacer to be in fixed mode, the program branches to the left and at 130 determines whether the pacemaker had previously been in the auto mode. If no, meaning that it was already in the fixed mode, the program proceeds directly to block 134. If yes, the program branches to block 132, where the actual onset is set equal to the standard onset value of zero, and the actual URth is likewise set equal to zero. At 134, it is determined whether a new onset parameter is to be selected for storage in the pacer. If no, the program goes directly to block 138, but if yes, it branches to 136. There the actual onset value is set equal to the reference onset value plus or minus a selected number of onset steps. In other words, onset parameter may be changed by as much as plus or minus two steps in any given day. After the physician makes the choice, the program proceeds to block 138. Here it is determined whether a new URth is desired. If no, the program proceeds directly to block 142, but if yes, it branches to block 140. At block 140, the reference URth is updated as a function of LRL and URL, and then the actual URth is changed to a value equal to the reference URth plus or minus a selected number of URth steps (again limited to two steps per day). By this means, the URth can be changed by external programming, to achieve a faster or slower approach at URL, but this change is limited to two steps (e.g., each step being 6 ms) in any day. Proceeding to block 142, the actual slope curve parameters A and B are derived from the reference curve, and then at block 144 the pacemaker is set into the fixed slope mode and the program exits.

Thus, there is provided a flexible pacemaker system for automatically adjusting rate response as a function of sensing change in at least one sensor input, at least pacing rate (or interval). In the preferred embodiment, changes are made in response to measurements at LRL and URL, but automatic adaptation can also be effected in different ways within the scope of the invention.

We claim:

1. A rate adaptive pacemaker system for pacing a patient, said system comprising a pacemaker having generator means for generating pacing pulses at a controlled pacing rate, any said pacing rate having a corresponding pacing interval, means for monitoring at least one patient variable correlative of desired heart rate, and rate control means for controlling said generator means to generate said pacing pulses at a rate which is a function of said at least one monitored variable, characterized by said rate control means comprising adjust means for automatically adjusting said function to correlate said pacing rate and said patient variable at at least one pacing rate in accordance with patient history.

2. The pacemaker system as described in claim 1, wherein said generator means generates pacing pulses at rates within a range limited by a lower rate limit (LRL) and an upper rate limit (URL), wherein said adjust means adjusts said function so that the correlation of said pacing rate and said patient variable is representative of patient history at at least two respective pacing rates.

3. The pacemaker system as described in claim 2, wherein one of said respective pacing rates is the LRL.

4. The pacemaker system as described in claim 2, wherein one of said respective pacing rates is the URL.

5. The pacemaker system as described in claim 1, wherein said correlation of said pacing rate and said patient variable is a variable defined as slope, and wherein said adjust means comprises stored values of slope for predetermined incremental pacing intervals.

6. The pacemaker system as described in claim 5, wherein said slope values are different corresponding to respective ones of said pacing intervals.

7. The pacemaker system as described in claim 2, comprising means for determining the LRL value of slope when it is a predetermined time of day and said pacemaker is operating at LRL.

8. The pacemaker system as described in claim 4, wherein said adjust means comprises means for adjusting the slope value at URL whenever URL is reached.

9. The pacemaker system as described in claim 4, wherein said adjust means comprises means for adjusting URL at least once within a predetermined time period.

10. The pacemaker system as described in claim 5, wherein said adjust means comprises means for continued monitoring of variations of said patient variable after said pacing rate reaches URL, and for adjusting said slope corresponding to URL in accordance with said continued monitored variations.

11. The pacemaker system as described in claim 1, wherein said adjust means comprises means for adjusting said function whenever the pacing rate corresponds to a predetermined rate.

12. The pacemaker system as described in claim 2, said pacemaker having means for inhibiting delivery of pacing signals in the presence of spontaneous heartbeats, and having overdrive means for delivering one or more pacing pulses during a time of sensing spontaneous heartbeats, thereby monitoring said at least one patient variable in the presence of spontaneous heartbeats.

13. A rate adaptive pacemaker system including a pacemaker and lead means for detecting pacing pulses and sensing heart signals, said pacemaker having generator means for delivering pacing pulses in the absence of spontaneous heartbeats, said pulses being delivered at rates between a lower rate level (LRL) and an upper rate level (URL), means for determining QT intervals of the patient, means for storing slope data representing a predetermined set of pacing intervals corresponding to respective QT intervals, means for adjusting the pacing rate of said delivered pacing signals as a function of said determined QT intervals and said stored data, and means for automatically determining the incremental change of pacing interval with respect to incremental change of QT at LRL and for changing said slope data to reflect said determined incremental changes.

14. The pacemaker system as described in claim 13, wherein said stored data represents a dynamic slope which corresponds to QT variations as a function of metabolic demand and pacing rate.

15. The pacemaker system as described in claim 13, further comprising means for adjusting said stored data to represent a decreased slope at URL whenever further shortening of QT is determined after pacing rate rises to URL.

16. The pacemaker system as described in claim 13, comprising adjusting slope by a predetermined incremental amount whenever a change in QT is determined.

17. The pacemaker system as described in claim 13, further having means for selecting said slope at URL from one of n stored values.

18. The pacemaker system as described in claim 13, said adjusting means further comprising means for adjusting said slope for values of pacing interval between LRL and URL as a function of determined slope at LRL and URL.

19. A method of pacing a patient with a rate adaptive implantable pacer, comprising:
setting lower rate limit (LRL) and upper rate limit (URL) limits on pacing rate,
monitoring at least one patient variable indicative of desired pacing rate for said patient,
controlling pacing rate as a dynamic function of said variable, said pacing rate being variable between said LRL and URL limits, and
automatically determining the value of said function at at least one of said limits, and adjusting said function to include said determined value.

20. The method according to claim 19, wherein said at least one of said limits is said URL limit, and comprising the further steps of determining when URL is reached and adjusting said function when URL has not been reached for a predetermined passage of time.

21. A rate adaptive pacemaker system for pacing a patient, said system comprising a pacemaker having generator means for generating pacing pulses at a controlled pacing rate, any said pacing rate having a corresponding pacing interval, means for monitoring at least one patient variable correlative of desired heart rate, and rate control means for controlling said generator means to generate said pacing pulses at a rate which is a function of said at least one monitored variable, wherein said function varies with pacing rate, and means for automatically determining said function at at least one pacing rate by testing patient response to pacing at said at least one rate, and means for adjusting said function in accordance with said determined function.

22. The pacemaker system as described in claim 21, wherein said adjusting means comprises means for adjusting said function throughout a predetermined pacing rate range.

* * * * *